(12) United States Patent
Ying et al.

(10) Patent No.: US 8,148,287 B2
(45) Date of Patent: Apr. 3, 2012

(54) CATALYST IMMOBILIZATION ON SILICEOUS MESOCELLULAR FOAM VIA CLICK CHEMISTRY

(75) Inventors: Jackie Y. Ying, Singapore (SG); Jaehong Lim, Singapore (SG); Su Seong Lee, Singapore (SG); Siti Nurhanna binte Riduan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/532,625

(22) PCT Filed: Mar. 20, 2008

(86) PCT No.: PCT/SG2008/000088
§ 371 (c)(1),
(2), (4) Date: Sep. 22, 2009

(87) PCT Pub. No.: WO2008/115154
PCT Pub. Date: Sep. 25, 2008

(65) Prior Publication Data
US 2010/0105544 A1      Apr. 29, 2010

Related U.S. Application Data

(60) Provisional application No. 60/907,134, filed on Mar. 22, 2007.

(51) Int. Cl.
*B01J 31/02*        (2006.01)
*B01J 31/28*        (2006.01)

(52) U.S. Cl. ........................................ 502/152; 502/158
(58) Field of Classification Search .................. None
See application file for complete search history.

(56) References Cited

U.S. PATENT DOCUMENTS
6,544,923 B1 *    4/2003    Huang et al. ................. 502/159

FOREIGN PATENT DOCUMENTS
WO    WO 2007/084075 A1    7/2007
WO    WO 2007/117221 A1    10/2007

OTHER PUBLICATIONS
SciFinder search history.*
Kolb, H.C. et al., "Click Chemistry: Diverse Chemical Function from a Few Good Reactions", Angewandte Chemie International Edition, Jun. 1, 2001, pp. 2004-2021, vol. 40, Issue 11.
Huisgen, R., "1,3-Dipolar Cycloadditions. Past and Future", Angewandte Chemie International Edition, Oct. 1963, pp. 565-598, vol. 2, Issue 10.
Lutz, J.-F., "1,3-Dipolar Cycloadditions of Azides and Alkynes: A Universal Ligation Tool in Polymer and Materials Science", Angewandte Chemie International Edition, Feb. 5, 2007, pp. 1018-1025, vol. 46, Issue 7.

(Continued)

*Primary Examiner* — Melvin Mayes
*Assistant Examiner* — Yun Qian
(74) *Attorney, Agent, or Firm* — Klarquist Sparkman, LLP

(57) ABSTRACT

The present invention relates to a method for preparing a heterogenised catalyst, comprising grafting a catalyst or catalyst precursor, via click chemistry, to a siliceous mesocellular foam (MCF). The invention also relates to a heterogenised catalyst comprising a catalyst species grafted onto a siliceous mesocellular foam (MCF) via a 1,2,3-triazole.

21 Claims, 1 Drawing Sheet

29a  X = -CH$_2$CH$_2$-
29b  X = -C$_6$H$_4$-

30a  X = -CH$_2$CH$_2$-
30b  X = -C$_6$H$_4$-

31a  X = -CH$_2$CH$_2$-
31b  X = -C$_6$H$_4$-

32a  X = -CH$_2$CH$_2$-
32b  X = -C$_6$H$_4$-

OTHER PUBLICATIONS

Hawker, C.J. and Wooley, K.L., "The Convergence of Synthetic Organic and Polymer Chemistries", Science, Aug. 19, 2005, pp. 1200-1205, vol. 309, No. 5738.

Binder, W.H. and Kluger, C., "AzIde/Alkyne—"Click" Reactions: Applications in Material Science and Organic Synthesis", Current Organic Chemistry, Sep. 2006, pp. 1791-1815, vol. 10, No. 14.

Corma, A. and Garcia, H., "Silica-Bound Homogenous Catalysts as Recoverable and Reusable Catalysts in Organic Synthesis", Advanced Synthesis & Catalysis, Aug. 2006, pp. 1391-1412, vol. 348, Issues 12-13.

Benaglia, M. et al., "Polymer-Supported Organic Catalysts", Chemical Reviews, Sep. 2003, pp. 3401-3430, vol. 103, Issue 9.

Fischer, D. and Blechert, S., "Highly Active Silica Gel-Supported Metathesis (Pre)Catalysts", Advanced Synthesis & Catalysis, Aug. 2005, pp. 1329-1332, vol. 347, Issue 10.

Corma, A. and Garcia, H., "Lewis Acids: From Conventional Homogenous to Green Homogenous and Heterogenous Catalysis", Chemical Reviews, Nov. 2003, pp. 4307-4366, vol. 103, Issue 11.

Corma, A. and Garcia, H., "Lewis Acids as Catalysts in Oxidation Reactions: From Homogenous to Heterogenous Systems", Chemical Reviews, Oct. 2002, pp. 3837-3892, vol. 102, Issue 10.

Schmidt-Winkel, P. et al., "Mesocellular Siliceous Foams with Uniformly Sized Cells and Windows", Journal of the American Chemical Society, Jan. 13, 1999, pp. 254-255, vol. 121, Issue 1.

Schmidt-Winkel, P. et al., "Microemulsion Templating of Siliceous Mesostructured Cellular Foams with Well-Defined Ultralarge Mesopores", Chemistry of Materials, Mar. 2000, pp. 686-696, vol. 12, Issue 3.

Lettow, J.S. et al., "Hexagonal to Mesocellular Foam Phase Transition in Polymer-Templated Mesoporous Silicas", Langmuir, Oct. 31, 2000, pp. 8291-8295, vol. 16, Issue 22.

Lettow, J.S. et al., "Small-Angle Neutron Scattering and Theoretical Investigation of Poly(ethylene oxide)-Poly(propylene oxide)-Poly-(ethylene oxide) Stabilized Oil-In-Water Microemulsions", Langmuir, Jun. 21, 2005, pp. 5738-5746, vol. 21, Issue 13.

Han, Y. and Ying, J.Y., "Generalized Fluorocarbon-Surfactant-Mediated Synthesis of Nanoparticles with Various Mesoporous Structures", Angewandte Chemie International Edition, 2005 (Dec. 27, 2004), pp. 288-292, vol. 44, Issue 2.

Lancaster, T.M. et al., "Effect of surface modification on the reactivity of MCF-supported IndaBOX", Chemical Communications, 2005, pp. 3577-3579, Issue 28.

Han, Y. et al., "Pressure-Driven Enzyme Entrapment in Siliceous Mesocellular Foam", Chemistry of Materials, Feb. 7, 2006, pp. 643-649, vol. 18, Issue 3.

Lee, S.S. et al, "Improved Enantioselectivity of Immobilized Chiral Bisoxazolines by Partial Precapping of the Siliceous Mesocellular Foam Support with Trimethylsilyl Groups", Advanced Synthesis & Catalysis, Jul. 2006, pp. 1248-1254, vol. 348, Issues 10-11.

Lee, S.S and Ting, J.Y., "Siliceous mesocellular foam-supported chiral bisoxazoline: Application to asymmetric cyclopropanation", Journal of Molecular Catalysis A: Chemical, Aug. 16, 2006, pp. 219-224, vol. 256, Issues 1-2.

Lim, J. et al., "Siliceous Mesocellular Foam-Supported Aza(bisoxaline)-Copper Catalysts", Advanced Synthesis & Catalysis, Jun. 9, 2008, pp. 1295-1308, vol. 350, Issue 9.

Ying, J.Y. et al., "Synthesis and Applications of Supramolecular-Templated Mesoporous Materials", Angewandte Chemie International Edition, Jan. 15, 1999, pp. 56-77, vol. 38, Issues 1-2.

Ying, Jackie Y., "Design and synthesis of nanostructured catalysts", Chemical Engineering Science, Mar. 2006, pp. 1540-1548, vol. 61, Issue 5.

Guo, Z. et al., "Click chemistry: a new facile and efficient strategy for preparation of functionalized HPLC packings", Chemical Communications, 2006, pp. 4512-4514, Issue 43.

Ortega-Muñoz, M. et al., "Synthesis of Glyco-Silicas by Cu(I)-Catalyzed "Click Chemistry" and their Applications in Affinity Chromatography", Advanced Synthesis & Catalysis, Nov. 2006, pp. 2410-2420, vol. 348, Issues 16-17.

Löber, S. et al., "Click Linker: Efficient and High-Yielding Synthesis of a New Family of SPOS Resins by 1,3-Dipolar Cycloaddition", Organic Letters, May 15, 2003, pp. 1753-1755, vol. 5, Issue 10.

Font, D. et al., "Polystyrene-Supported Hydroxyproline: An Insoluble, Recyclable Organocatalyst for the Asymmetric Aldol Reaction in Water", Organic Letters, Sep. 28, 2006, pp. 4653-4655, vol. 8, Issue 20.

Deiters, A. and Martin, S.F., "Synthesis of Oxygen- and Nitrogen-Containing Heterocycles by Ring-Closing Metathesis", Chemical Reviews, May 2004, pp. 2199-2238, vol. 10, Issue 5.

Thayer, A., "Removing Impurities: Metal scavengers and immobilized catalysts may make for cleaner pharmaceutical products", Chemical & Engineering News, Sep. 5, 2005, pp. 55-58, vol. 83, No. 36.

Yao, Qingwei, "A Soluble Polymer-Bound Ruthenium Carbene Complex: A Robust and Reusable Catalyst for Ring-Closing Olefin Metathesis", Angewandte Chemie International Edition, Nov. 3, 2000, pp. 3896-3898, vol. 39, Issue 21.

Kingsbury, J.S. et al., "Immobilization of Olefin Metathesis Catalysts on Monolithic Sol—Gel: Practical, Efficient, and Easily Recyclable Catalysts for Organic and Combinational Synthesis", Angewandte Chemie International Edition, Nov. 19, 2001, pp. 4251-4256, vol. 40, Issue 22.

Kingsbury, J.S. et al,. "A Recyclable Ru-Based Metathesis Catalyst", Journal of the American Chemical Society, Feb. 3, 1999, pp. 791-799, vol. 121, Issue 4.

Ghosh, A.K. et al., "C2-Symmetric chiral bis(oxazoline)-metal complexes in catalytic asymmetric synthesis", Tetrahedron: Assymetry, Jan. 16, 1998, pp. 1-45, vol. 9, Issue 1.

Pfaltz, A., "From Corrin Chemistry to Asymmetric Catalysis—A Personal Account", Synlett, Jun. 1999, pp. 835-842, Issue Supplement 1.

Johnson, J.S. and Evans, D.A., "Chiral Bis(oxazoline) Copper(II) Complexes: Versatile Catalysts for Enantioselective Cycloaddition, Aldol, Michael and Carbonyl Ene Reactions", Accounts of Chemical Research, Jun. 2000, pp. 325-335, vol. 33, Issue 6.

Fache, F. et al., "Nitrogen-Containing Ligands for Asymmetric Homogeneous and Heterogeneous Catalysis", Chemical Reviews, Jun. 2000, pp. 2159-2231, vol. 100, Issue 6.

Rechavi, D. and Lemaire, M., "Enantioselective Catalysis Using Heterogeneous Bis(oxazoline) Ligands: Which Factors Influence the Enantioselectivity?", Chemical Reviews, Oct. 2002, pp. 3467-3494, vol. 102, Issue 10.

Glos, M. and Reiser, O., "Aza-bis(oxazolines): New Chiral Ligands for Asymmetric Catalysis", Organic Letters, Jul. 13, 2000, pp. 2045-2048, vol. 2, Issue 14.

Werner, H. et al., "Synthesis of Polymer Bound Azabis(oxazoline) Ligands and their Application in Asymmetric Cyclopropanations", Advanced Synthesis & Catalysis, Jan. 2006, pp. 125-132, vol. 348, Issues 1-2.

Werner, H. et al., "Improved Synthesis of Aza-bis(oxazoline) Ligands", The Journal of Organic Chemistry, Dec. 26, 2003, pp. 10166-10168, vol. 68, Issue 26.

Cozzi, F., "Immobilization of Organic Catalysts: When, Why, and How", Advanced Synthesis & Catalysis, Aug. 2006, pp. 1367-1390, vol. 348, Issues 12-13.

Kobayashi, S. and Akiyama, R., "Renaissance of Immobilized catalysts, New types of polymer-supported catalysts, 'microencapsulated catalysts', which enable environmentally benign and powerful high-throughput organic synthesis", Chemical Communications, 2003, pp. 449-460, Issue 4.

Lee, B.S. et al., "Novel method for catalyst immobilization using an ionic polymer: a case study using recyclable ytterbium triflate", Tetrahedron Letters, Jan. 31, 2005, pp. 807-810, vol. 46, Issue 5.

Zhang, Y. et al., "Enantioselective Catalysis over Chiral Imidazolidin-4-one Immobilized on Siliceous and Polymer-Coated Mesocellular Foams", Advanced Synthesis & Catalysis, Oct. 2006, pp. 2027-2032, vol. 348, Issue 15.

Ahrendt, K.A. et al., "New Strategies for Organic Catalysis: The First Highly Enantioselective Organocatalytic Diels—Alder Reaction", Journal of the American Chemical Society, May 3, 2000, pp. 4243-4244, vol. 122, Issue 17.

Jen, W.S. et al., "New Strategies for Organic Catalysis: The First Enantioselective Organocatalytic 1,3-Dipolar Cycloaddition", Journal of the American Chemical Society, Oct. 11, 2000, pp. 9874-9875, vol. 122, Issue 40.

Northrup, A.B. and MacMillan, D.W.C., "The First General Enantioselective Catalytic Diels-Alder Reaction with Simple alpha,beta-Unsaturated Ketones", Journal of the American Chemical Society, Mar. 20, 2002, pp. 2458-2460, vol. 124, Issue 11.

Paras, N.A. and MacMillan, D.W.C., "The Enantioselective Organocatalytic 1,4-Addition of Electron-Rich Benzenes to alpha,beta-Unsaturated Aldehydes", Journal of the American Chemical Society, Jul. 10, 2002, pp. 7894-7895, vol. 124, Issue 27.

Austin, J.F. and MacMillan, D.W.C., "Enantioselective Organocatalytic Indole Alkylations. Design of a New and Highly Effective Chiral Amine for Iminium Catalysis", Journal of the American Chemical Society, Feb. 20, 2002, pp. 1172-1173, vol. 124, Issue 7.

Brown, S.P. et al., "The First Enantioselective Organocatalytic Mukaiyama—Michael Reaction: A Direct Method for the Synthesis of Enantioenriched gamma-Butenolide Architecture", Journal of the American Chemical Society, Feb. 5, 2003, pp. 1192-1194, vol. 125, Issue 5.

Puglisi, A. et al., "Enantioselective 1,3-Dipolar Cycloadditions of Unsaturated Aldehydes Promoted by A Poly (ethylene glycol)-Supported Organic Catalyst", European Journal of Organic Chemistry, Feb. 2004, pp. 567-573, Issue 3.

Benaglia, M. et al., "Poly(ethylene glycol)-Supported Chiral Imidazolldin-4-one: An Efficient Organic Catalyst for the Enantioselective Diels-Alder Cycloaddition", Advanced Synthesis & Catalysis, Feb. 2002, pp. 149-152, vol. 344, Issue 2.

Selkälä, S.A. et al., "Asymmetric Organocatalytic Diels-Alder Reactions on Solid Support", Advanced Synthesis & Catalysis, Oct. 2002, pp. 941-945, vol. 344, Issue 9.

Anastas, P.T. et al., "The role of catalysis in the design, development, and implementation of green chemistry", Catalysis Today, Jan. 5, 2000, pp. 11-22, vol. 55, Issues 1-2.

Sheldon, R., "Green Chemistry—one year on", Green Chemistry, Feb. 2000, pp. G1-G4, vol. 2, Issue 1.

Dioos, B. et al., "Aspects of Immobilisation of Catalysts on Polymeric Supports", Advanced Synthesis & Catalysis, Aug. 2006, pp. 1413-1446, vol. 348, Issue 12-13.

International Search Report & Written Opinion (International Application No. PCT/SG2008/000088), mailed Jun. 13, 2008.

International Preliminary Report on Patentability (International Application No. PCT/SG2008/000088), issued Sep. 22, 2009.

Extended European Search Report dated Mar. 31, 2010 (issued in EP Application No. 08724352.3), Mar. 31, 2010.

Park, J.K. et al., "Heterogeneous asymmetric Diels-Alder reactions using a copper-chiral bis(oxazoline) complex immobilized on mesoporous silica", Tetrahrdron: Asymmetry, Nov. 26, 2001, pp. 2931-2935, vol. 12, Issue 21.

Kacprzak, K.M. et al., "Highly efficient immobilization of Cinchona alkaloid derivatives to silica gel via click chemistry", Tetrahedron Letters, Dec. 4, 2006, pp. 8721-8726, vol. 47, Issue 49.

* cited by examiner

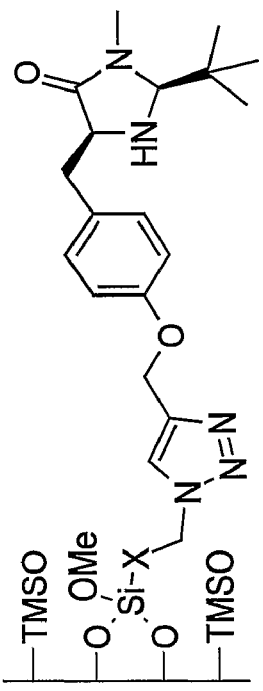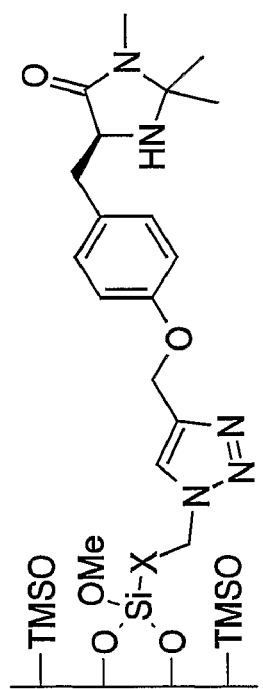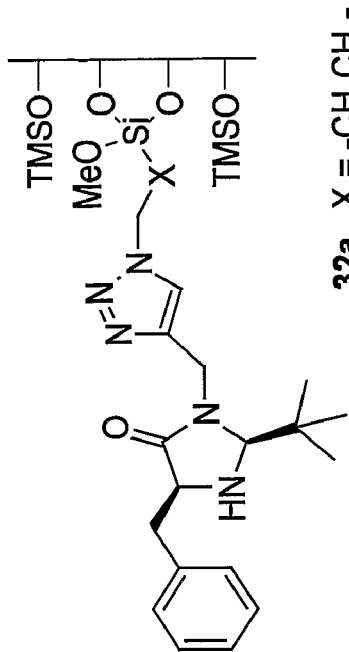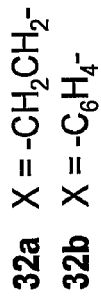

CATALYST IMMOBILIZATION ON SILICEOUS MESOCELLULAR FOAM VIA CLICK CHEMISTRY

CROSS REFERENCE TO RELATED APPLICATION

This application claims benefit of, and priority from, U.S. provisional patent application No. 60/907,134, filed on Mar. 22, 2007, the contents of which are fully incorporated herein by reference.

FIELD OF THE INVENTION

This invention relates to the application of "click chemistry" for the immobilisation of catalysts on siliceous mesocellular foams (MCF).

BACKGROUND OF THE INVENTION

Sharpless and co-workers first introduced the concept of "click chemistry",[1] employing powerful and selective reactions for the efficient synthesis of interesting compounds and materials through heteroaromatic links, e.g., Huisgen 1,3-dipolar cycloaddition of azides and alkynes.[2] This modular process is reliable, widely applicable, of high yield, and requires only simple reaction and purification conditions. It does not involve reagents that are difficult to handle, and is stable towards strong bases.[3]

Recently, applications of "click chemistry" were reported in the synthesis of chemically and biologically useful materials.[4,5] However, the development of heterogenized catalysts has seemingly produced the most significant impact on the chemical and pharmaceutical industries.[6,7] Although attempts to immobilise homogeneous catalytic complexes (not via click chemistry) on various supports have been reported[7-4], these have not always generated sufficiently effective heterogenized catalysts for industrial applications. Immobilised catalysts (also referred to herein as heterogenised catalysts) can offer a number of advantages, such as ease of catalyst recovery and products isolation, reduced production costs, and decreased catalyst contamination of products, etc.[8,9] Such systems are of great interest given the growing demands of inexpensive green chemistry.[32]

BRIEF SUMMARY OF THE INVENTION

In one aspect, the present invention provides a method for preparing a heterogenised catalyst, comprising grafting a Catalyst or catalyst precursor, via click chemistry, to a siliceous mesocellular foam (MCF).

In another aspect, the present invention provides a heterogenised catalyst comprising a catalyst species grafted onto a siliceous mesocellular foam (MCF) via a 1,2,3-triazole.

The above and other features and advantages of the present invention will become apparent from the following description when taken in conjunction with the accompanying figures which illustrate preferred embodiments of the present invention by way of example.

BRIEF DESCRIPTION OF THE DRAWINGS

Embodiments of the invention will be discussed with reference to the following FIGURE:

FIG. 1 displays the structures of four heterogenised organocatalysts.

DETAILED DESCRIPTION OF THE INVENTION

Click chemistry has been adopted for the immobilisation of several types of compounds on different supports, including silica. However, the beneficial combination of click chemistry and siliceous mesocellular foam (MCF) has not been explored previously for the development of heterogenised catalysts with high cost efficiency, environmental compatibility, and catalytic activity. The present invention provides a facile and inexpensive method for the preparation of efficient and reusable catalyst systems, which method is widely applicable to a variety of ligands, catalysts, solvents, and supports. The MCF microparticles can also be easily tailored in terms of microstructure, pore size and surface chemistry for specific applications.

Click Chemistry

Click chemistry is a chemical philosophy that describes chemistry tailored to generate substances quickly and reliably by joining small units together. Generally, click chemistry encourages reactions that have modular applications that are wide in scope, that have a high chemical yield, that generate inoffensive by-products, that are stereospecific, that require simple reaction conditions, that use readily available starting materials and reagents, that are solvent free or use benign solvents such as water, that lead to easy product isolation by crystallisation or distillation but not preparative chromatography, that have a large thermodynamic driving force to favour a reaction with a single reaction product, and that have a high atom economy. While certain of the general criteria can be subjective in nature, and not all criteria need to be met, several reactions are generally recognised as "click chemistry" reactions. Examples of such include the Huisgen 1,3-dipolar cycloaddition and variants thereof.

The azide-alkyne Huisgen cycloaddition is a 1,3-dipolar cycloaddition between an azide and a terminal or internal alkyne to give a 1,2,3-triazole. This reaction can be exemplified as follows:

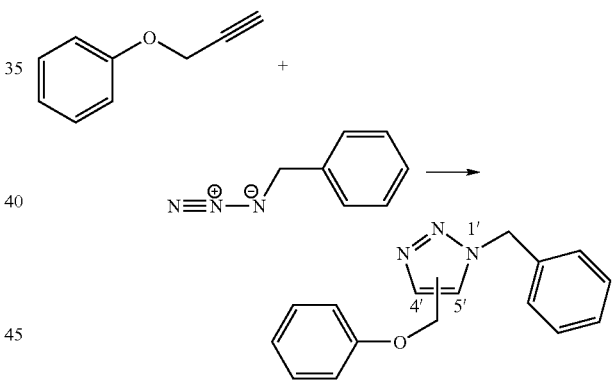

In the reaction above the azide reacts with the alkyne to afford the triazole as a mixture of 1,4-adduct and 1,5-adduct.

A notable variant of the Huisgen 1,3-dipolar cycloaddition is the copper(I) catalysed variant, in which organic azides and terminal alkynes are united to afford 1,4-regioisomers of 1,2,3-triazoles as sole products. The reaction can be performed using commercial sources of copper(I), such as cuprous bromide or iodide, or with other copper sources such as a mixture of copper(II) (e.g. copper(II) sulfate) and a reducing agent (e.g. sodium ascorbate) to produce Cu(I) in situ. As Cu(I) is unstable in aqueous solvents, stabilising ligands, such as tris-(benzyltriazolylmethyl)amine (TBTA), can be used. The reaction can be carried out in a variety of solvents, examples of which include mixtures of water with a variety of miscible or partially miscible organic solvents such as alcohols, DMSO, DMF, tBuOH and acetone.

In one embodiment of the above reactions, the terminal alkyne can be protected with a trimethyl silyl protecting group, followed and subsequent deprotection after the radical reactions are complete.

Siliceous Mesocellular Foam

Siliceous MCF microparticles serve as an excellent support material, and click chemistry provides a highly reliable and widely applicable tool for the grafting of catalytic complexes.

Siliceous mesocellular foam (MCF)[10] has been found to be a very useful support material for heterogenised catalysts.[11] The physical and chemical robustness of MCF allow this material to be easily handled both at the laboratory and manufacturing scales. These foams facilitate reactions involving bulky substrates without diffusion limitations, and can be used to host large catalytic complexes without steric hindrance.[12] Hence, it is advantageous to use this mesoporous silica material as a solid support in combination with click chemistry to develop novel heterogenized catalysts.[13,14]

Siliceous mesocellular foams can be prepared according to known methods, such as those taught in international publication No. WO/2006/135339, the contents of which are incorporated herein by reference.

The foam may comprise cell-like mesopores connected by windows of a smaller size. The mean pore size (e.g. cell pore size) may be greater than about 5 nm, or greater than about 10 nm. It may be between about 5 and about 100 nm or between about 5 and 50, 5 and 20, 10 and 30, 50 and 100, 20 and 30, 20 and 25, 2 and 22, 24 and 42, 25 and 30, 27 and 30, 27 and 29, or 10 and 50 nm. The pore size may be about 5, 10, 15, 20, 21, 22, 23, 24, 25, 26, 27, 28, 29, 30, 35, 40, 45, 50, 55, 60, 65, 70, 75, 80, 85, 90, 95 or 100 nm. The ratio of the size of the mesopores and the size of the windows may be between about 10:1 and about 1.5:1, or between about 10:1 and 2:1, 10:1 and 5:1, 5:1 and 1.5:1, 3:1 and 1.5:1, 5:1 and 3:1 or 8:1 and 4:1, and may be about 10:1, 9:1, 8:1, 7:1, 6:1, 5:1, 4.5:1, 4:1, 3.5:1, 3:1, 2.5:1, 2:1 or 1.5:1, or may be some other ratio. The size of the windows (i.e. window pore size) may be greater than about 2 nm, greater than 5 nm, or greater than about 10 nm. It may be between about 2 and about 100 nm or between about 2 and 50, 2 and 10, 5 and 50, 5 and 20, 10 and 20, 10 and 15, and 12, 15 and 20, 15 and 18, 15 and 17, 10 and 100, 50 and 100 or 10 and 50 nm. The window size may be about 2, 3, 4, 5, 10, 11, 12, 13, 14, 15, 16, 17, 18, 19, 20, 25, 30, 35, 40, 45, 50, 55, 60 65, 70, 75, 80, 85, 90, 95 or 100 nm. The particles may have a distribution of different window sizes. The different window sizes may be between about 2 and 100 nm. In one embodiment, the mean pore size is between 24 and 42 nm and the windows connecting the pores have a diameter from 9 to 22 nm.

The particles of regular shaped solid foam may have a mean particle diameter of between about 1 and about 20 microns, or between about 2 and about 50, 20 and 50, 10 and 50, 2 and 40, 1 and 10, 1 and 5, 1 and 2, 2 and 20, 2 and 10, 3 and 8, 4 and 7, 4 and 6, 5 and 20, 10 and 20, 2 and 10 or 5 and 10 microns, and may have a mean particle diameter of about 1, 2, 3, 4, 5, 6, 7, 8, 9, 10, 11, 12, 13, 14, 15, 16, 17, 18, 19-20, 25, 30, 35, 40, 45 or 50 microns, or may be less than 1 micron or greater than 50 microns. The particles of solid foam may have a narrow particle size distribution or the particles may have a distribution of different pore sizes. There may be less than about 50% of particles having a particle size more than 10% different from (greater than or less than) the mean particle size, or there may be less than about 45, 40, 35, 30, 25, 20, 15, 10 or 5% of particles having a particle size more than 10% different from the mean particle size, and may be about 1, 2, 3, 4, 5, 10, 15, 20, 25, 30, 35, 40, 45 or 50% of particles having a particle size more than 10% different from the mean particle size.

The particles may have a pore volume of between about 0.5 and about 5 cm$^3$/g, or between about 0.5 and 4, 0.5 and 3, 0.5 and 2, 1 and 5, 2 and 5, 3 and 5, 1 and 3, 1 and 2, 2 and 3, 1.5 and 2, 1.5 and 1.7, 2 and 2.5, 2.2 and 2.4 or 2 and 2.4, and may have a pore volume about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5 or 5 cm$^3$/g or more than about 5 cm$^3$/g. The particles may gave a specific surface area of between about 100 and about 1000 m$^2$/g, or between about 100 and 500, 100 and 200, 200 and 1000, 500 and 1000, 200 and 800, 200 and 500, 500 and 800, 500 and 700, 500 and 600, 550 and 600, 550 and 570, 600 and 800, 650 and 750, 670 and 730 or 690 and 710 m$^2$/g, and may have a specific surface area of about 100, 150, 200, 250, 300, 350, 400, 450, 500, 510, 520, 530 540, 550, 560, 570, 580, 590, 600, 610, 620, 630, 640, 650, 660, 670, 680, 690, 700, 710, 720, 730, 750, 750, 800, 850, 900 950 or 1000 m$^2$/g, or may have a specific surface area of less than about 100 or greater than about 1000 m$^2$/g.

The foam may comprise silica, aluminosilicate or silica doped with a metal such as aluminium, tin or lead. The foam may comprise mesoporous silica.

The particles of solid foam may be spherical, or they may be some other shape, such as ovoid, ellipsoid, cubic, rhomboidal, prismatic, or parallelepiped (for example rectangular parallelepiped). The particles may be hydrophilic or they may be hydrophobic. If they are hydrophobic, they may have alkyl groups (for example alkylsilyl groups) or aryl groups (for example from arylsilyl groups) on their surfaces. The alkyl groups may comprise $C_1$ to $C_{20}$ straight chain or branched alkyl groups, for example methyl, ethyl, octyl, octadecyl or isopropyl. The arylsilyl groups may comprise for example phenyl or tolyl groups. The particles of solid foam may have trimethylsilyl groups on their surfaces.

Method for Obtaining Heterogenised Catalysts

The methods of the invention offer environmentally friendly and often less costly synthesis options for chemicals and pharmaceuticals. Further, heterogenised catalysts obtained by the methods exhibit excellent activity and reusability, with tolerance to a range of substrates and reaction media.

The methods of the invention can be used to obtain a variety of heterogenised catalysts; both metal-based catalysts (i.e. organometallic catalysts) and non-metal catalysts (i.e. organocatalysts).

In one embodiment, heterogenised catalysts comprising one or more metal atoms are prepared by grafting, by click chemistry, a catalyst precursor such as a ligand (that bears or has been derivatised to bear a chemical group suitable for click chemistry) to the siliceous MCF, and to then combine the immobilised ligand with the metal species, optionally together with further ligand molecules. In another embodiment, a fully or partially formed metal-comprising catalyst, which comprises a ligand having a chemical group suitable for click chemistry, is grafted onto the siliceous MCF (optionally followed by further reactions to complete the catalyst species if a partially formed metal-bearing catalyst is grafted). In a further embodiment, a catalyst which does not contain a metal atom (also referred to herein as an organocatalyst) can be derivatised such that it bears a chemical group suitable for click chemistry, and then grafted onto the siliceous MCF.

In one embodiment, the catalyst or catalyst precursor can be grafted to the siliceous MCF by way of a linker moiety. For example, the linker moiety can bear an alkyne group or an azide group, along with a group that can react with the siliceous MCF. The linker can then be reacted with the catalyst or catalyst precursor (which will bear an alkyne group or an azide group, as appropriate) by way of a 1,3-dipolar cycloaddition reaction to form an intermediate, which intermediate is then reacted with the siliceous MCF. Alternatively, the linker moiety can be reacted to the siliceous MCF to form an intermediate, which intermediate is then reacted with the catalyst or catalyst precursor by way of a 1,3-dipolar cycloaddition reaction.

Examples of suitable linker moieties include molecules that comprise an azide or an alkyne group, together with a group that can react with the siliceous MCF. Examples of such groups include trialkoxy silyl groups, e.g. trimethoxy silyl. In one embodiment, the linker moiety can have the formula:

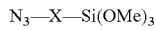

wherein X is —CH$_2$CH$_2$— or —C$_6$H$_4$—.

Any type of catalyst can be used in the present invention, as long as it comprises or can be derivatised to comprise a chemical group suitable for click chemistry. Examples of suitable types of catalysts include ring-closing metathesis catalysts, cyclopropanation catalysts, and organocatalysts such as amino acids. Specific examples of suitable catalysts for use with the methods of the invention are provided below.

EXAMPLES

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

Ring-Closing Metathesis

Ring-closing metathesis (RCM) has played a key role in the generation of various cyclic motifs.[15] However, the pharmaceutical industry has not yet widely utilized RCM in large-scale manufacturing due largely to the high cost of the ruthenium-containing compounds, and the significant metal leaching problem. For example, Ruthenium residue levels must be less than 5 ppm and 0.5 ppm for oral and parental drug products, according to the guidelines of European Agency for the Evaluation of Medicinal Products[16]. Although many research groups have reported on the immobilization of the first- and second-generation Grubbs' catalysts on various supports,[17] these heterogenized catalysts suffer from shortcomings such as low activity due to diffusion-related issues, reduced activity upon reuse, and requirement for further purification.[18]

The preparation of immobilized ruthenium catalysts for RCM is depicted in Scheme 1.

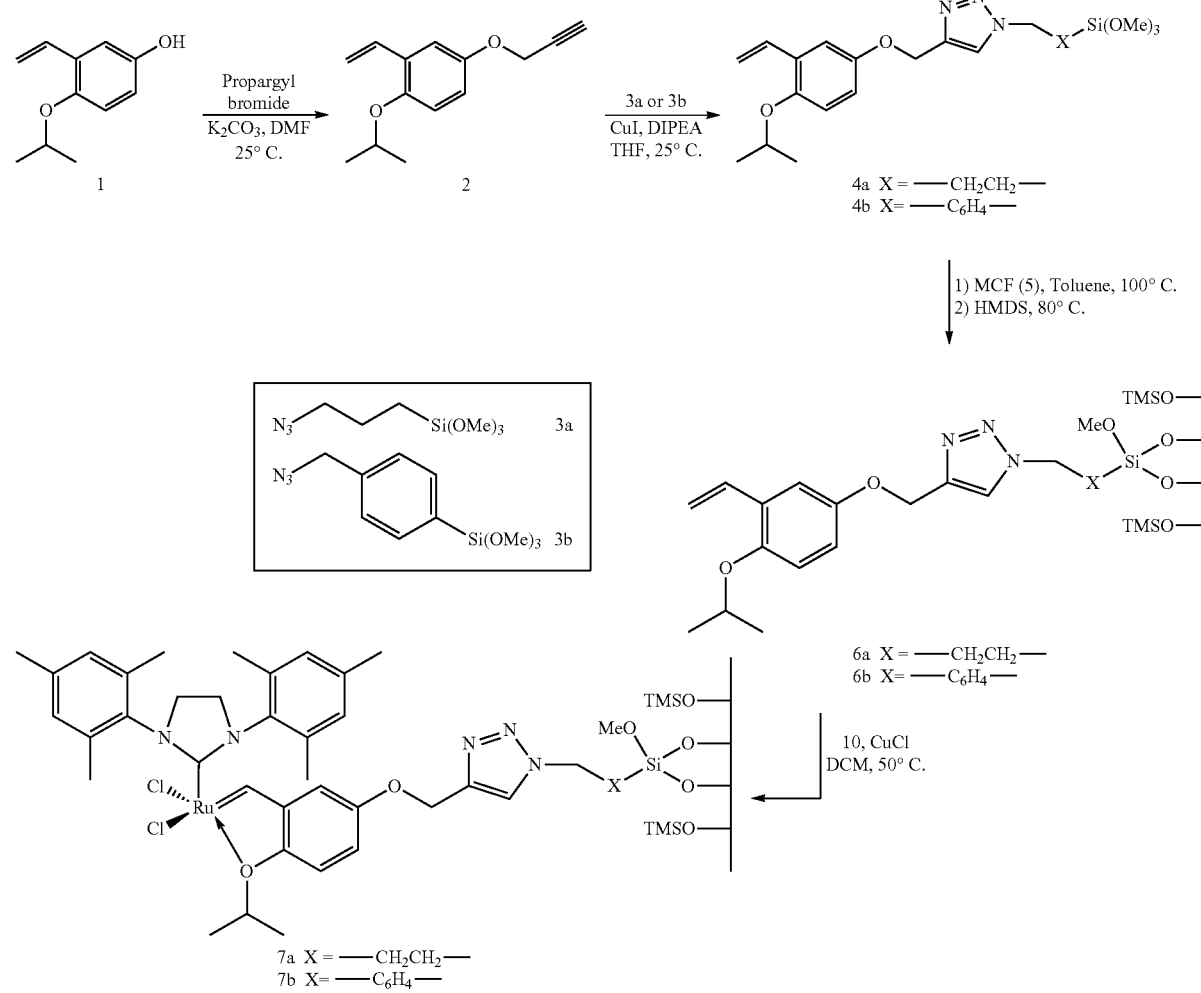

Alkyne 2 was readily prepared from the known phenol 1[18] by propargylation under mild conditions. Treatment of 2 with 3a/b freshly prepared from the corresponding bromides produced the triazoles 4a/b in the presence of Cu(I) iodide. The Hoveyda-Grubbs type ligands were smoothly grafted onto partially trimethylsilyl (TMS)-precapped MCF at 100° C. in toluene to provide the immobilized ligands 6a/b, whose structures were confirmed by photoacoustic Fourier-transform infrared (PA-FTIR) and cross-polarization magic angle spinning (CPMAS) $^{13}$C nuclear magnetic resonance (NMR) spectra.

The green powders were isolated by treating the commercially available second-generation Grubbs catalyst and the functionalized MCF 6a/b in refluxing dichloromethane (DCM) in the presence of Cu(I) chloride,[19] followed by filtration and drying. The incorporation of ruthenium onto the immobilized ligand 6a/b was accomplished in good yields.

Table 1 summarizes the loading densities of ligand in 6a/b and ruthenium in 7a/b, respectively.

TABLE 1

| Entry | Catalyst | Ligand in 6[a] (mmol/g) | Ru in 7[a] (mmol/g) | Ru/ligand ratio |
|---|---|---|---|---|
| 1 | 7a | 0.19 | 0.16 | 0.9 |
| 2 | 7b | 0.19 | 0.16 | 0.9 |

[a]Determined by elemental analysis.

These numbers could be easily controlled by the ratio of 4a/b and Grubbs catalyst. The heterogenized ruthenium catalysts 7a/b exhibited good activity and recyclability, and were stored for more than several months without activity loss.[20]

The activity of heterogenized catalysts 7a/b was tested for RCM by using diethyl diallylmalonate 8 as the benchmark substrate. The diene 8 was smoothly and completely transformed into the cyclised product 9 within 1.5 h by using 5 mol % of 7a/b in DCM at ambient temperature without forming noticeable side-products, as indicated by NMR spectroscopy (Table 2).

TABLE 2

$$\text{8} \xrightarrow[\text{DCM, 25° C.}]{\text{5 mol \% cat.}} \text{9}$$
(c = 0.05 M)

| Entry | Catalyst | 0 h | 0.25 h | 0.50 h | 0.75 h | 1.00 h | 1.25 h | 1.50 h |
|---|---|---|---|---|---|---|---|---|
| 1 | 7a | 0 | 59 | 86 | 97 | 99 | 100 | — |
| 2 | 7b | 0 | 44 | 78 | 88 | 97 | 99 | 100 |
| 3 | 10 | 0 | 84 | 98 | 99 | 100 | — | — |

[a]Determined by gas chromatography (GC).

The immobilised catalysts 7a/b proved to be less efficient than the commercially available second-generation Hoveyda-Grubbs catalyst (10). However, the reaction rate could be enhanced by tuning the linker moiety in 7a/b. The more flexible propyl linker led to faster conversion, while the more rigid benzyl counterpart exhibited slower conversion. These differences were not significant, however.

Excellent recyclability of 7a/b was demonstrated in Table 3, particularly at an elevated temperature associated with the reduced reaction time.

TABLE 3

$$\text{8} \xrightarrow[\text{DCM, 25° C.}]{\text{5 mol \% cat.}} \text{9}$$
(c = 0.05 M)

| | | | Conversion in each run (%)[b] | | | | |
|---|---|---|---|---|---|---|---|
| Entry | Catalyst | Conditions | Run 1 | Run 3 | Run 5 | Run 7 | Run 10 |
| 1 | 7a | 50° C., 0.5 h | 99 | 96 | 94 | 91 | 91 |
| 2 |    | 25° C., 1.5 h | 99 | 96 | 94 | 89 | 69 |
| 3 | 7b | 50° C., 0.5 h | 100 | 98 | 98 | 93 | 91 |
| 4 |    | 25° C., 1.5 h | 100 | 95 | 94 | 88 | 78 |

These results correlated well to our previous results with the carbamate linkers.[11e]

Example 2

Preparation of RCM Ligand 2

A Schlenk flask was charged with phenol 1 (10.0 mmol), propargyl bromide (12.0 mmol), potassium carbonate (12.0 mmol), and dried DMF (20 ml) under argon. The reaction mixture was stirred at 60° C. for 12 h. Upon complete conversion of 1 by thin layer chromatography (TLC), the resulting mixture was cooled to room temperature and diluted with ethyl acetate (100 ml), washed with water (2×50 ml) and brine (50 ml) successively. The organic layer was dried over magnesium sulfate, and concentrated under reduced pressure. A flash column chromatography (hexane:ethyl acetate=4:1) gave alkyne 2 (8.20 mmol) as a colourless oil. $^1$H-NMR (400 MHz, CDCl$_3$): δ 1.33 (d, 6H, J=6.0 Hz), 2.54 (t, 1H, J=1.8 Hz), 4.42 (septet, 1H, J=6.0 Hz), 4.67 (d, 2H, J=1.8 Hz), 5.26 (dd, 1H, J=11.2, 1.2 Hz), 5.72 (dd, 1H, J=17.6, 1.2 Hz), 6.85 (bs, 2H), 7.05 (dd, 1H, J=17.6, 11.2 Hz), 7.13 (bs, 1H). $^{13}$C-NMR (100 MHz, CDCl$_3$): δ 22.2, 55.5, 72.1, 75.4, 78.8, 112.7, 114.4, 115.2, 116.5, 129.2, 131.6, 150.1, 151.8.

Example 3

Preparation of RCM Catalysts 7a and 7b

Click Chemistry Reaction

A Schlenk flask was charged with alkyne 2 (0.50 mmol), trimethoxysilane 3a (0.50 mmol), Cu(I) iodide (5 μmol), and N,N'-diisopropylethylamine (DIPEA) (1.00 mmol) in THF (5 ml). The resulting mixture was stirred at ambient temperature for 12 h under argon. The volatile components were completely removed under reduced pressure to give the triazole 4a as a colourless oil in a quantitative yield, which was used for the next step without further purification. $^1$H-NMR (400 MHz, CDCl$_3$): δ 0.61-0.65 (m, 2H), 1.32 (d, J=6.0 Hz, 6H), 2.04 (quintet, 2H, J=7.6 Hz), 3.57 (s, 9H), 4.37 (t, J=7.6 Hz, 2H), 4.40 (septet, J=6.0 Hz, 1H), 5.20 (s, 2H), 5.25 (dd, 1H, J=11.2, 1.2 Hz), 5.72 (dd, 1H, J=17.6, 1.2 Hz), 6.85 (bs, 2H), 7.04 (dd, 1H, J=17.6, 11.2 Hz), 7.14 (d, 1H, J=2.4 Hz), 7.62 (s, 1H). $^{13}$C-NMR (100 MHz, CDCl$_3$): δ 6.2, 22.2, 24.0, 50.7, 52.5, 62.7, 72.1, 112.5, 114.4, 114.9, 116.7, 122.6, 129.3, 131.6, 144.3, 149.8, 152.5. MS (FAB): m/z (%) 422 (100) [M$^+$+H], 453 (10), 268 (14).

The general procedure for click chemistry using 2 (0.50 mmol) and 3b (0.50 mmol) gave 4b. $^1$H-NMR (400 MHz, CDCl$_3$): δ 1.32 (d, J=6.0 Hz, 6H), 3.63 (s, 9H), 4.40 (septet, J=6.0 Hz, 1H), 5.18 (s, 2H), 5.25 (dd, 1H, J=11.2, 1.2 Hz), 5.56 (s, 2H), 5.69 (dd, 1H, J=17.6, 1.2 Hz), 6.83 (bs, 2H), 7.03 (dd, 1H, J=17.6, 11.2 Hz), 7.11 (bs, 1H), 7.31 (d, 2H, J=7.6 Hz), 7.67 (d, 2H, 7.6 Hz). $^{13}$C-NMR (100 MHz, CDCl$_3$): δ 22.2, 50.9, 54.1, 62.7, 72.1, 112.6, 114.4, 114.9, 116.6, 122.6, 127.5, 129.3, 130.4, 131.6, 135.6, 136.8, 145.0, 149.9, 152.4. MS (FAB): m/z (%) 470 (100) [M$^+$+H], 264 (10), 211 (73). HRMS (FAB) calculated for C$_{24}$H$_{32}$N$_3$O$_5$Si: 470.2106 [M$^+$+H], found 470.2098.

Ligand Grafting

A Schlenk flask was charged with the TMS-precapped MCF 5 (2.00 g, 0.60 mmol TMS/g), and placed under vacuum for 24 h at 120° C. The flask was purged with argon at room temperature, and charged with dried toluene (40 ml) and trimethoxysilane 4a (0.50 mmol). The resulting mixture was heated for 24 h at 90° C. Upon cooling to room temperature, the solid was thoroughly rinsed by toluene, DCM, methanol, and DCM (50 ml each). The white solid was transferred to a Schlenk flask, and dried under vacuum for 12 h at 80° C. After cooling down to room temperature, the flask was placed in liquid nitrogen bath for 10 min, and HMDS (1 ml) was added at −200° C. under vacuum. The flask was sealed, and then kept at 80° C. for 5 h. The resulting solid was cooled to room temperature, washed thoroughly with DCM (100 ml), and then dried under vacuum for 24 h to give the immobilised ligand 6a as a white powder. $^{13}$C CP-MAS NMR: δ 3.64, 13.3, 23.8, 27.3, 54.5, 65.7, 74.5, 115.0, 119.5, 124.8, 132.9, 135.4, 147.8, 153.2, 156.5. Elemental analysis, found: C, 9.16; H, 1.90; N, 0.87. Loading of ligand: 0.19 mmol/g.

The general procedure for ligand grafting using 5 (2.00 g, 0.60 mmol TMS/g) and 4b (0.50 mmol) gave 6b. Elemental analysis, found: C, 9.98; H, 1.85; N, 0.85. Loading of ligand: 0.19 mmol/g.

Ruthenium Loading

A two-necked flask equipped with a reflux condenser was charged with ligand 6a (2.00 g, 0.19 mmol/g), second-generation Grubbs' catalyst (0.38 mmol), copper chloride (0.38 mmol), and dried DCM (20 ml) under argon. The reaction mixture was heated for 5 h under reflux in argon. The reaction mixture gradually changed from dark brown to deep green. After cooling to room temperature, the fine powder was washed thoroughly with DCM (100 ml) under open atmosphere, and dried under vacuum for 24 h to give the immobilised catalyst 7a as a green powder. Elemental analysis, found: C, 12.65; H, 2.15; N, 1.23. Loading of ruthenium: 0.16 mmol/g.

The general procedure for ruthenium loading using 6b (2.00 g, 0.19 mmol/g) gave 7b. Elemental analysis, found: C, 13.47; H, 2.13; N, 1.29. Loading of ruthenium: 0.16 mmol/g.

Testing Catalytic Activity for RCM

Reactions were run in a vial containing a magnetic stir bar in argon at room temperature. The vial was charged with catalysts 6a/b (5 μmol) and DCM (2 ml). The substrate 8 (0.10 mmol) was injected via a syringe. The conversions were monitored by GC after filtration through a short pad of silica gel by elution with DCM.

Testing Catalyst Recyclability for RCM

Reactions were run in a similar manner as described above. On completion of each run, the reaction vial was centrifuged at 4000 rpm for 3 min. The supernatant was characterised by GC for conversion. The vial was charged with another aliquot of DCM, stirred for 1 min, and centrifuged again. One more rinse was performed before the next run was conducted with fresh substrate.

Example 4

Cyclopropanation

Chiral bisoxazolines (BOX) have demonstrated high selectivity for various asymmetric catalytic reactions.[21] However, the corresponding organometallic catalysts suffered from low turnover numbers (TON) in achieving the high enantioselectivity. Thus, there has been a great deal of interest to immobilise these catalysts on various supports.[22,23] Click chemistry was adopted for immobilizing azabisoxazoline (azaBOX) onto MCF, not merely as a tool for combining two small molecules, but as a protocol for grafting.

The known amine 11[24] was readily prepared and reacted with propargyl bromide to give the alkyne 12, mediated by sodium hydride in tetrahydrofuran (THF). This relatively unstable ligand was immediately "clicked" with 3a/b in the presence of Cu(I) iodide to give the triazoles 13a/b in quantitative yields, whose structures were elucidated by PA-FTIR and CPMAS $^{13}$C-NMR spectra (Scheme 2).

Scheme 2

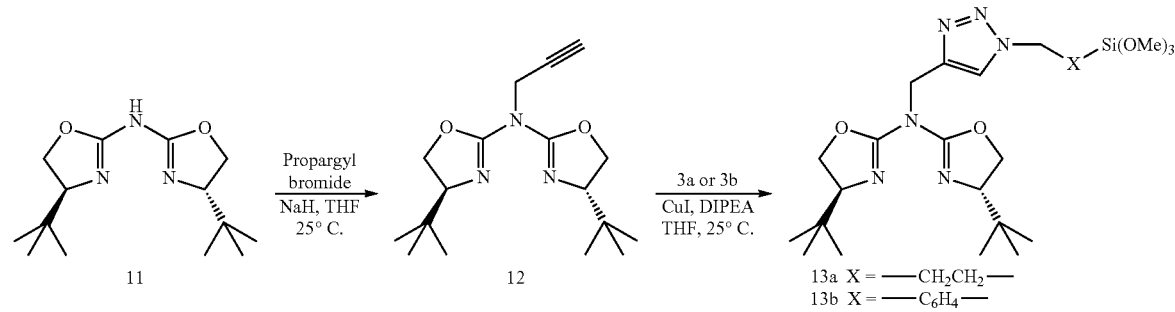

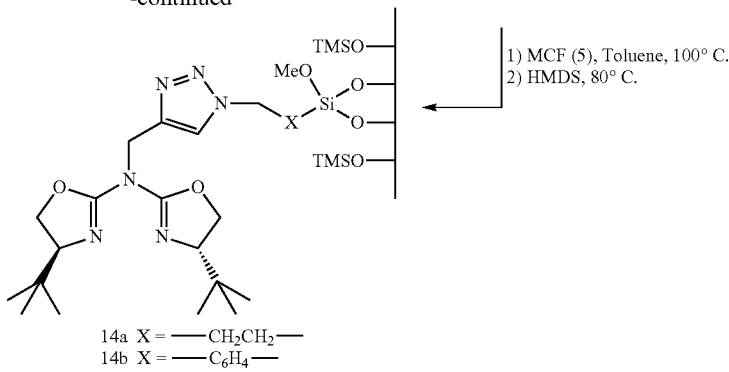

14a X = —CH₂CH₂—
14b X = —C₆H₄—

The precursors 13a/b were smoothly grafted at an elevated temperature in toluene onto TMS-precapped MCF (5). The preparation of the MCF-supported azaBOX 14a/b was completed by postcapping the remaining silanol via treatment with hexamethyldisilazane (HMDS) in vapor phase.

Starting from 11, the overall yields of 14a/b were over 70%. Introduction of metal was accomplished by adding Cu(II) triflate into a THF suspension of 14a/b. After stirring for 1 h, the suspension was filtered, washed with THF thoroughly, and dried under vacuum to produce the corresponding Cu(II) complexes (15a/b).

Cyclopropanation was performed over Cu(I) complexes, which were generated in situ by reducing Cu(II) complexes with phenylhydrazine (PhNHNH₂) (Scheme 3).

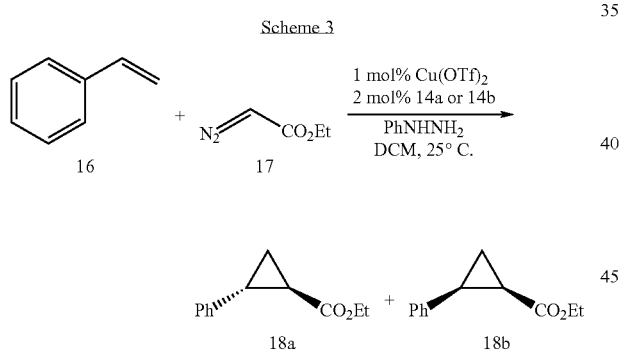

In the formation of cyclopropane 17a/b, excellent enantioselectivity and recyclability were achieved by utilising our immobilised Cu-azaBOX complexes.

A more facile synthesis of 15a/b was examined by performing grafting and complexation in one pot using a stoichiometric amount of Cu(I). The immobilised azide 19a/b was readily prepared by condensation of 3a/b and 5 in toluene, followed by postcapping with TMS group (Scheme 4).

Scheme 4

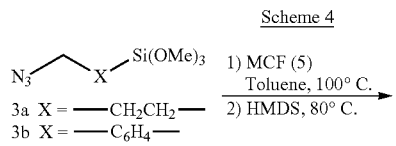

3a X = —CH₂CH₂—
3b X = —C₆H₄—

1) MCF (5)
   Toluene, 100° C.
2) HMDS, 80° C.

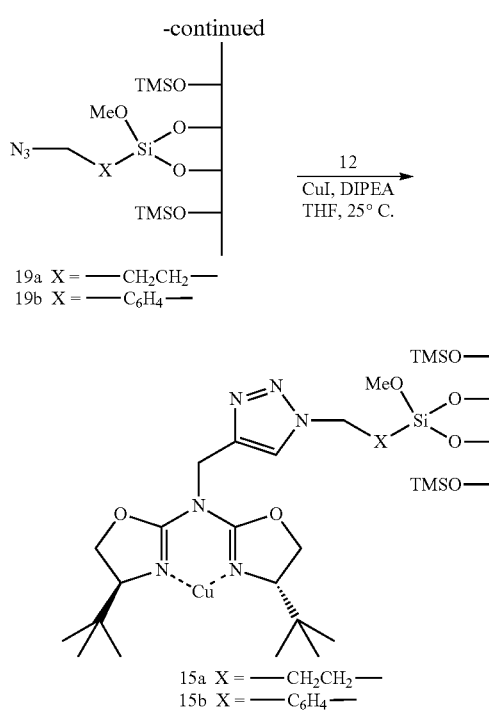

19a X = —CH₂CH₂—
19b X = —C₆H₄—

15a X = —CH₂CH₂—
15b X = —C₆H₄—

The complexes 15a/b were smoothly formed by reacting 12 and 19a/b in the presence of >0.5 equivalent of Cu(I) iodide in THF. A tandem reaction of triazole formation and Cu(I) complexation significantly facilitated the preparation of azaBOX-based heterogenised catalysts for enantioselective cyclopropanation.

Example 5

Preparation of BOX Ligand 12

Amine 11 (10.0 mmol) in THF (10 ml) was added slowly at ambient temperature to a Schlenk flask charged with sodium hydride (12.0 mmol) as a suspension in THF (20 ml). The resulting mixture was stirred at 60° C. for 1 h, and then cooled to ambient temperature prior to the addition of propargyl bromide (13.0 mmol) in argon. The reaction mixture was stirred for 12 h. On complete conversion of 1 by TLC, the resulting mixture was filtered through a short pad of Celite™ and concentrated under reduced pressure. A flash column chromatography (hexane:ethyl acetate=4:1) gave alkyne 12

(7.80 mmol). $^1$H-NMR (400 MHz, CDCl$_3$): δ 0.91 (s, 18H), 2.25 (t, J=2.4 Hz, 1H), 3.84 (dd, J=6.4, 9.2 Hz, 2H), 4.30 (dd, J=6.4, 8.4 Hz, 2H), 4.38 (dd, J=8.4, 9.2 Hz, 2H), 4.69 (d, J=2.4 Hz, 2H). $^{13}$C-NMR (100 MHz, CDCl$_3$): δ 24.5, 34.1, 39.9, 70.7, 71.5, 73.2, 79.4, 156.5.

Example 6

Preparation of the BOX Ligand 14a and 14b

The general procedure for click chemistry using 12 (0.80 mmol) and 3a (0.75 mmol) gave 13a. $^1$H-NMR (400 MHz, CDCl$_3$): δ 0.60-0.65 (m, 2H), 0.85 (s, 18H), 1.97-2.00 (m, 2H), 3.57 (s, 9H), 3.79-3.83 (m, 2H), 4.24 (t, J=6.4 Hz, 2H), 4.28-4.40 (m, 4H), 5.15 (bs, 2H), 7.63 (s, 1H). $^{13}$C-NMR (100 MHz, CDCl$_3$): δ6.2, 24.0, 24.8, 25.5, 34.0, 50.6, 52.3, 70.2, 73.4, 122.9, 144.5, 157.0. MS (FAB): m/z (%) 511 (100) [M$^+$+H], 453 (10), 268 (14). HRMS (FAB) calculated for C$_{23}$H$_{43}$N$_6$O$_5$Si: 511.3059 [M$^+$+H], found 511.3047.

The general procedure for click chemistry using 12 (0.80 mmol) and 3b (0.75 mmol) gave 13b. $^1$H-NMR (400 MHz, CDCl$_3$): δ 0.79 (s, 18H), 3.63 (s, 9H), 3.77 (dd, J=6.8, 9.2 Hz, 2H), 4.20 (dd, J=6.8, 8.0 Hz, 2H), 4.30 (dd, J=8.0, 9.2 Hz, 2H), 5.14 (s, 2H), 5.49 (bs, 2H), 7.27 (d, J=8.4 Hz), 7.64 (d, J=8.4 Hz). $^{13}$C-NMR (100 MHz, CDCl$_3$): δ 24.8, 25.5, 33.9, 50.9, 54.0, 70.2, 73.4, 122.9, 127.6, 130.2, 135.5, 137.0, 145.0, 157.0. MS (FAB): m/z (%) 559 (100) [M$^+$+H], 306 (10), 268 (23). HRMS (FAB) calculated for C$_{27}$H$_{43}$N$_6$O$_5$Si: 559.3059 [M$^+$+H], found 559.3051.

The general procedure for ligand grafting using 5 (2.50 g, 0.80 mmol TMS/g) and 13a (0.75 mmol) gave 14a. Elemental analysis, found: C, 9.36; H, 1.99; N, 2.00. Loading of ligand: 0.24 mmol/g.

The general procedure for ligand grafting using 5 (2.50 g, 0.80 mmol TMS/g) and 13b (0.75 mmol) gave 14b. Elemental analysis, found: C, 10.29; H, 1.94; N, 1.70. Loading of ligand: 0.21 mmol/g.

Procedure for Cyclopropanation

Cu(II) triflate (10 µmol) was added to 14a (20 µmol) dispersed in THF. After stirring for 1 h, the suspension was filtered, washed with THF, and then dried under vacuum to give 15a. Dodecane (0.5 mmol) and phenylhydrazine (25 µl of a 5% solution) were added to a suspension of 15a in DCM (3 ml). After addition of styrene (1.5 mmol), ethyl diazoacetate (1.0 mmol) in DCM (2 ml) was introduced dropwise over 5 h using a syringe pump. The mixture was stirred for an additional 2 h, and centrifuged. The solution portion was collected, and the trans/cis ratio and yield were determined by GC. The enantiomeric excess was determined by GC using a Chiraldex-B column. The precipitate was washed with DCM (5 ml) and centrifuged. The same rinsing procedure was repeated three times. The recovered catalyst was reused directly for the next run.

Example 7

Organocatalysis

Organocatalysts[25] are attractive as they offer less expensive and environmentally benign processes. They may also be more readily amenable than metal-based catalysts to anchoring on a support for catalyst reuse.[25] The immobilisation of a metal-based catalyst on a support (generally achieved by anchoring an organic ligand followed by metal addition) is often plagued by metal leaching problems, and requires catalyst regeneration by metal replenishment before reuse.[26]

Amino acids and their derivatives represent an obvious source of chiral organocatalysts.[25] Their availability and different functionalities in the residues allow for a number of applications in the field of supported catalysis.[27]

Recently, protonated phenylalanine-derived cyclic amines have emerged as versatile organic catalysts.[28] Imidazolidin-4-ones, originally proposed as organocatalysts by MacMillan and co-workers, have found widespread use in a number of processes.[29] Their relevance led several groups to develop soluble and insoluble supported catalysts to promote the enantioselective Diels-Alder cycloaddition, 1,3-dipolar cycloaddition, and Friedel-Crafts alkylation, etc.[27,30]

The preparation of immobilized imidazolidin-4-ones is illustrated in Scheme 5.

Scheme 5

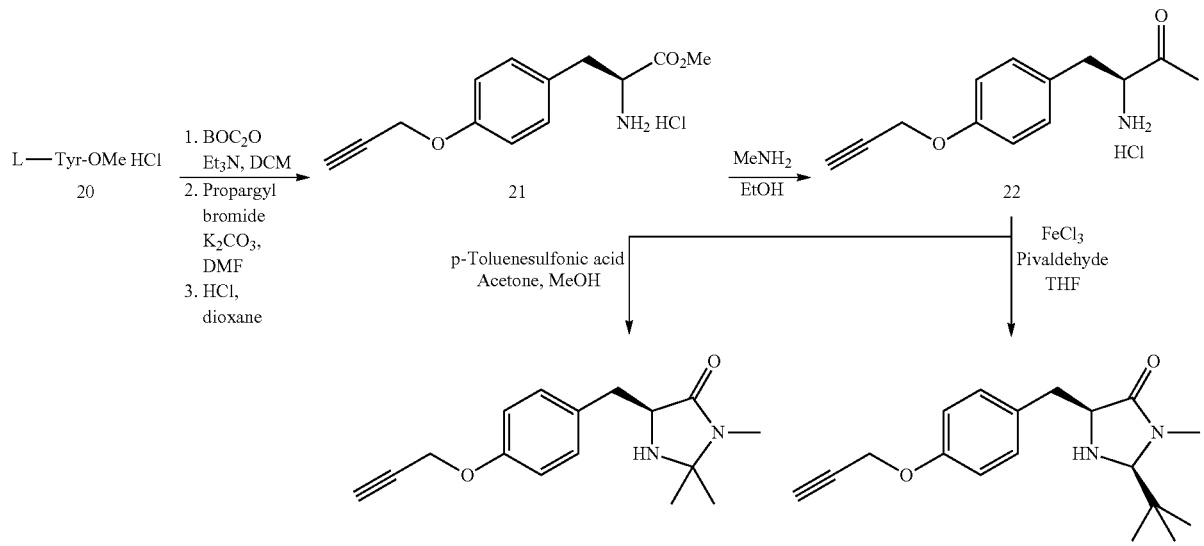

Starting from tyrosine methyl ester hydrochloride (20), of which free hydroxyl group would play a key part as a linkage to MCF, the alkynes 23 and 24 were synthesized in good yields by following the reported scheme (Scheme 5).[28a,31] Phenylalanine served as an alternative source of immobilized chiral imidazolidinones. A triple bond was successfully introduced by condensation of 25 and propargylamine in solvent-free conditions (Scheme 6).

Scheme 6

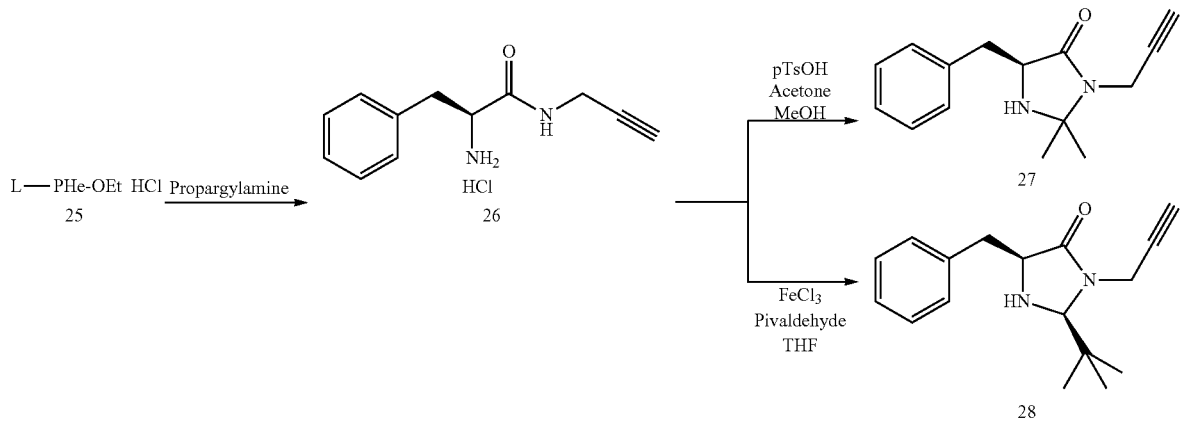

According to our previous synthetic methods, the alkynes 23/24/27/28 were further modified to append trimethoxysilane group by "clicking" with 3a/b prior to the grafting onto MCF. These heterogenized organocatalysts 29-32 in FIG. 1 proved to be useful for several reactions, providing good efficiency and selectivity as well as high recyclability.

Example 8

Preparation of Immobilised Organocatalysts 29-32

The general procedure for ligand grafting using 5 (2.00 g, 0.60 mmol TMS/g) and a click chemistry product from the corresponding precursors 23 and 3a (0.50 mmol, each) gave 29a. Elemental analysis, found: C, 9.03; H, 1.89; N, 1.14. Loading of catalyst: 0.16 mmol/g.

The general procedure for ligand grafting using 5 (2.00 g, 0.60 mmol TMS/g) and a click chemistry product from the corresponding precursors 27 and 3a (0.50 mmol, each) gave 31a. Elemental analysis, found: C, 8.82; H, 1.91; N, 1.15. Loading of catalyst: 0.16 mmol/g.

All publications, patents and patent applications cited in this specification are herein incorporated by reference as is each individual publication, patent or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a", "an", and "the" include plural reference unless the context clearly dictates otherwise. Unless defined otherwise all technical and scientific terms used herein have the same meaning as commonly understood to one of ordinary skill in the art to which this invention belongs.

REFERENCES

[1] H. C. Kolb, M. G. Finn, K. B. Sharpless, *Angew. Chem. Int. Ed.* 2001, 40, 2004.
[2] R. Huisgen, *Angew. Chem. Int. Ed.* 1963, 2, 565.
[3] For a recent review, see: J.-F. Lutz, *Angew. Chem. Int. Ed.* 2007, 46, 1018.
[4] C. J. Hawker, K. L. Wooley, *Science* 2005, 309, 1200.
[5] W. H. Binder, C. Kluger, *Curr. Org. Chem.* 2006, 10, 1791.
[6] For a recent review on silica-supported catalysts, see: A. Corma, H. Garcia, *Adv. Synth. Catal.* 2006, 348, 1391.
[7] For a review on polymer-supported catalysts, see: M. Benaglia, A. Puglisi, F. Cozzi, *Chem. Rev.* 2003, 103, 3401.
[7A] e.g. D. Fischer, S. Blechert, *Adv. Synth. Catal.* 2005, 347, 1329.
[8] A. Corma, H. Garcia, *Chem. Rev.* 2003, 103, 4307.
[9] A. Corma, H. Garcia, *Chem. Rev.* 2002, 102, 3837.
[10] a) P. Schmidt-Winkel, W. W. Lukens, Jr., D. Zhao, P. Yang, B. F. Chmelka, G. D. Stucky, *J. Am. Chem. Soc.* 1999, 121, 254; b) P. Schmidt-Winkel, W. W. Lukens, Jr., P. Yang, D. I. Margolese, J. S. Lettow, J. Y. Ying, G. D. Stucky, *Chem. Mater.* 2000, 12, 686; c) J. S. Lettow, Y. J. Han, P. Schmidt-Winkel, P. Yang, D. Zhao, G. D. Stucky, J. Y. Ying, *Langmuir* 2000, 16, 8291; d) J. S. Lettow, T. M. Lancaster, C. J. Glinka, J. Y. Ying, *Langmuir* 2005, 21, 5738; e) H. Yu, J. Y. Ying, *Angew. Chem. Int. Ed.* 2005, 44, 288. f) Y. Han, S. S. Lee, J. Y. Ying, *Chem. Mater.*, in press.
[11] a) T. M. Lancaster, S. S. Lee, J. Y. Ying, *Chem. Commun.* 2005, 3577. b) Y. Han, S. S. Lee, J. Y. Ying, *Chem. Mater.* 2006, 18, 643. c) S. S. Lee, S. Hadinoto, J. Y. Ying, *Adv. Synth. Catal.* 2006, 348, 1248. d) S. S. Lee, J. Y. Ying, *J. Mol. Catal. A: Chem.* 2006, 256, 219. e) J. Lim, S. S. Lee, S, N. Riduan, J. Y. Ying, *Adv. Synth. Catal.*, in press.
[12] a) J. Y. Ying, C. P. Mehnert, M. S. Wong, *Angew. Chem. Int. Ed.* 1999, 38, 56; b) J. Y. Ying, *Chem. Eng. Sci.* 2006, 61, 1540.

[13] For recent papers on the application of click chemistry on silica, see: a) Z. Guo, A. Lei, X. Liang, Q. Xu, *Chem. Commun.* 2006, 4512; b) M. Ortega-Munoz, J. Lopez-Jaramillo, F. Hernandez-Mateo, F. Santoyo-Gonzalez, *Adv. Synth. Catal.* 2006, 348, 2410.

[14] For recent papers on the application of click chemistry on polymer, see: a) S. Löber, P. Rodriguez-Loaiza, P. Gmeiner, *Org. Lett.* 2003, 5, 1753; b) D. Font, C. Jimeno, M. A. Pericàs, *Org. Lett.* 2006, 8, 4653.

[15] For a recent review, see: A. Deiters, S. F. Martin, *Chem. Rev.* 2004, 104, 2199.

[16] A. Thayer, *Chem. Eng. News* 2005, 83, 55.

[17] For an example, see: Q. Yao, *Angew. Chem. Int. Ed.* 2000, 39, 3896.

[18] J. S. Kingsbury, S. B. Garber, J. M. Giftos, B. L. Gray, M. M. Okamoto, R. A. Farrer, J. T. Fourkas, A. H. Hoveyda, *Angew. Chem. Int. Ed.* 2001, 40, 4251.

[19] J. S. Kingsbury, J. P. A. Harrity, P. J. Bonitatebus, Jr., A. H. Hoveyda, *J. Am. Chem. Soc.* 1999, 121, 791.

[20] For other studies on Ru catalyst decomposition and longevity, see [19] and references cited therein.

[21] a) A. K. Gosh, P. Mathivanan, J. Capiello, *Tetrahedron: Asymmetry* 1998, 9, 1; b) A. Pfaltz, *Synlett* 1999, 835; c) J. S. Johnson, D. A. Evans, *Acc. Chem. Res.* 2000, 32, 325; d) F. Fache, E. Schulz, M. L. Tommasino, M. Lemaire, *Chem. Rev.* 2000, 100, 2159.

[22] D. Rechavi, M. Lemaire, *Chem. Rev.* 2000, 100, 2159.

[23] a) M. Glos, O. Reiser, *Org. Lett.* 2000, 2, 2045; b) H. Werner, C. I. Herrerías, M. Glos, A. Gissibl, J. M. Fraile, I. Pérez, J. A. Mayoral, O. Reiser, *Adv. Synth. Catal.* 2006, 348, 125.

[24] H. Werner, R. Vicha, A. Gissibl, O. Reiser, *J. Org. Chem.* 2003, 68, 10166.

[25] F. Cozzi, *Adv. Synth. Catal.* 2006, 348, 1367.

[26] For a review on microencapsulation, see: S. Kobayashi, R. Akiyama, *Chem. Commun.* 2003, 449. For recent applications of ionic polymers, see: B. S. Lee, S. Mahajan, K. D. Janda, *Tetrahedron Lett.* 2005, 46, 807.

[27] Y. Zhang, L. Zhao, S. S. Lee, J. Y. Ying, *Adv. Synth. Catal.* 2006, 348, 2027.

[28] K. A. Ahrendt, C. J. Borths, D. W. C. MacMillan, *J. Am. Chem. Soc.* 2000, 122, 4243; b) W. S. Jen, J. J. M. Wiener, D. W. C. MacMillan, *J. Am. Chem. Soc.* 2000, 122, 9874.

[29] For Diels-Alder cycloadditions, see [28a]; a) A. B. Northrup, D. W. C. MacMillan, *J. Am. Chem. Soc.* 2002, 124, 2458. For nitrone cycloadditions, see [28b]. For Friedel-Crafts alkylations, see: b) N. A. Paras, D. W. C. MacMillan, *J. Am. Chem. Soc.* 2002, 124, 7894, and references cited therein; c) J. F. Austin, D. W. C. MacMillan, *J. Am. Chem. Soc.* 2002, 124, 1172. For Mukaiyama-Michael reactions, see: d) S. P. Brown, N. C. Goodwin, D. W. C. MacMillan, *J. Am. Chem. Soc.* 2003, 125, 1192.

[30] Besides [27], see: a) A. Puglisi, M. Benaglia, M. Cinquini, F. Cozzi, G. Celentano, *Eur. J. Org. Chem.* 2004, 567; b) M. Benaglia, G. Celentano, M. Cinquini, A. Puglisi, F. Cozzi, *Adv. Synth. Catal.* 2002, 344, 149; c) S. A. Selkälä, J. Tois, P. M. Pihko, A. M. P. Koskinen, *Adv. Synth. Catal.* 2002, 344, 941.

[31] N. A. Paras, D. W. C. MacMillan, *J. Am. Chem. Soc.* 2002, 124, 7894.

[32] a) P. T. Anastas, L. B. Bartlett, M. M. Kirchhoff, T. C. Williamson, *Catal. Today* 2000, 55, 11; b) R. A. Sheldon, *Green Chem.* 2000, 2, G1.

The invention claimed is:

1. A method for preparing a heterogenised catalyst, comprising grafting a catalyst or catalyst precursor, via click chemistry, to a siliceous mesocellular foam (MCF) via a 1,2,3-triazole, said heterogenised catalyst being:

(i) a ring-closing metathesis catalyst having the formula

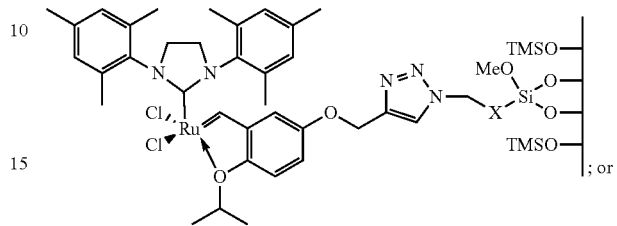

(ii) an organocatalyst that is a protonated phenylalanine-derived cyclic amine grafted to the MCF via the 1,2,3-triazole; and imidazolidin-4-one grafted to the MCF via the 1,2,3-triazole; or has the formula:

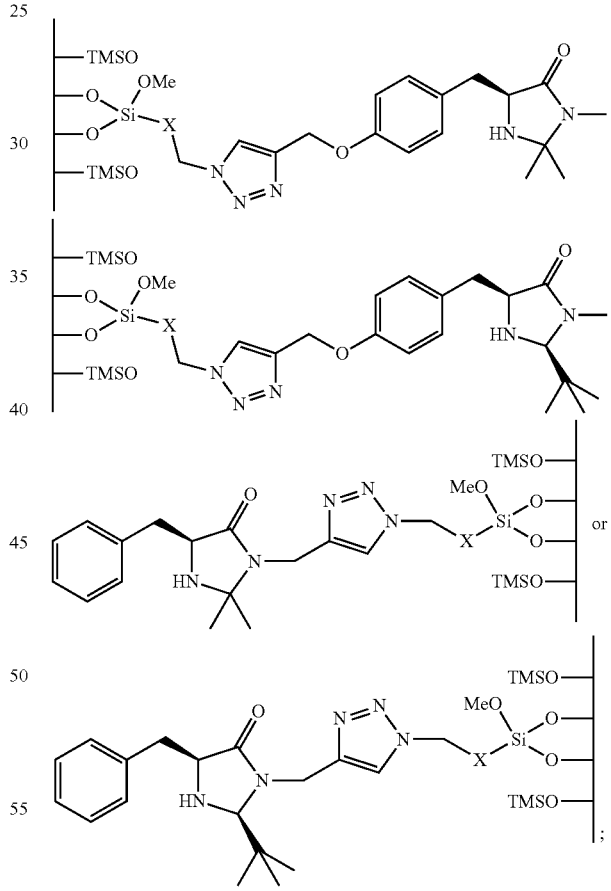

wherein —X— is —$CH_2CH_2$— or —$C_6H_4$—.

2. A method according to claim 1, wherein the grafting is effected at least in part by a 1,3-dipolar cycloaddition reaction.

3. A method according to claim 2, wherein the 1,3-dipolar cycloaddition reaction is between an alkyne group and an azide group.

4. A method according to claim 2, wherein the 1,3-dipolar cycloaddition is carried out in the presence of a copper catalyst.

5. A method according to claim 4, wherein the copper catalyst comprises
(a) a source of copper(I), or
(b) a source of copper(II), and a reducing agent.

6. A method according to claim 1, wherein the catalyst or catalyst precursor is grafted to the siliceous MCF by way of a linker moiety.

7. A method according to claim 6, wherein
the catalyst or catalyst precursor bears an alkyne group,
the linker moiety beam an azide group and a group that can react with the siliceous MCF, and
the grafting is carried out by reacting the catalyst or catalyst precursor to the linker moiety by way of 1,3-dipolar cycloaddition reaction to form an intermediate, which intermediate is then reacted with the siliceous MCF.

8. A method according to claim 6, wherein
the catalyst or catalyst precursor bears an alkyne group,
the linker moiety bears an azide group and a group that can react with the siliceous MCF, and
the grafting is carried out by reacting the siliceous MCF to the linker moiety to form an intermediate, which intermediate is then reacted with the catalyst or catalyst precursor by way of a 1,3-dipolar cycloaddition reaction.

9. A method according to claim 6, wherein the linker moiety has the formula:

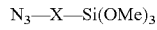

wherein X is —$CH_2CH_2$— or —$C_6H_4$—.

10. A method according to claim 6, wherein
the catalyst or catalyst precursor bears an azide group,
the linker moiety bears an alkyne group and a group that can react with the siliceous MCF, and
the grafting is carried out by reacting the catalyst or catalyst precursor to the linker moiety by way of a 1,3-dipolar cycloaddition reaction to form intermediate, which intermediate is then reacted with the siliceous MCF.

11. A method according to claim 6, wherein
the catalyst or catalyst precursor bears an azide group,
the linker moiety bears an alkyne group and a group that can react with the siliceous MCF, and
the grafting is carried out by reacting the siliceous MCF to the linker moiety to form an intermediate, which intermediate is then reacted with the catalyst or catalyst precursor by way of a 1,3-dipolar cycloaddition reaction.

12. A method according to claim 1, wherein the catalyst precursor is a ligand suitable to form an organometallic ring-closing metathesis catalyst.

13. A method according to claim 1, wherein the catalyst is an imidazolidin-4-one derivative comprising an alkyne group or and azide group.

14. A method according to claim 1, comprising a further step of converting the catalyst precursor to a catalyst.

15. A method according to claim 14, wherein the catalyst precursor is a ligand, and the converging step comprises reacting the catalyst precursor with a metal species and optionally further ligand molecules to form a heterogenised organometallic catalyst.

16. A heterogenised catalyst obtained by grafting a catalyst or catalyst precursor, via click chemistry, to a siliceous mesocellular foam (MCF), said catalyst grafted to the MCF via a 1,2,3-triazole, said heterogenised catalyst being;

(i) a ring-closing metathesis catalyst having, the formula

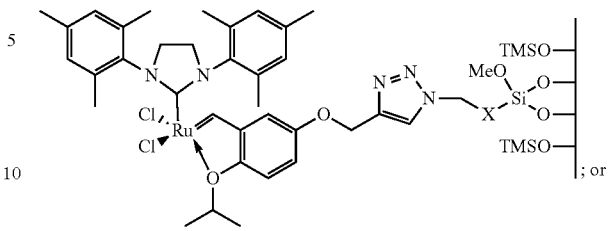

; or (ii) an organocatalyst that is a protonated phenylalanine-derived cyclic amine grafted to the MCF via the 1,2,3-triazole; an imidazolidin-4-one grafted to the MCF via the 1,2,3-triazole; or has the formula;

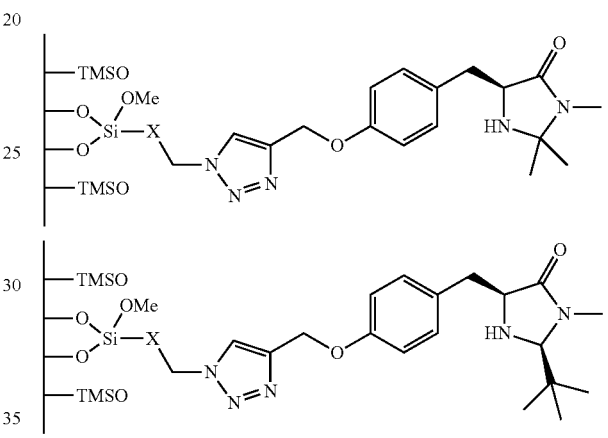

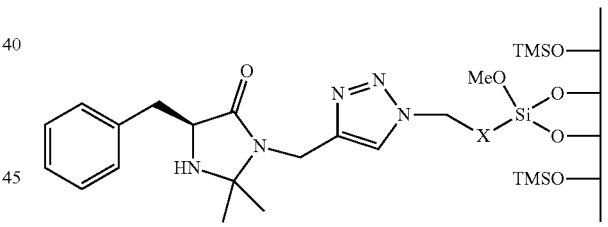

or

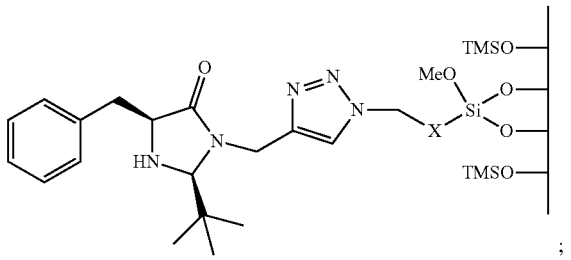

;

wherein —X— is —$CH_2CH_2$— or —$C_6H_4$—.

17. A heterogenised catalyst according to claim 16, wherein the catalyst species is grafted onto the siliceous MCF through a 1,4-adduct or a 1,5-adduct of the 1,2,3-triazole.

18. The heterogenised catalyst according to claim 16, which has the formula:

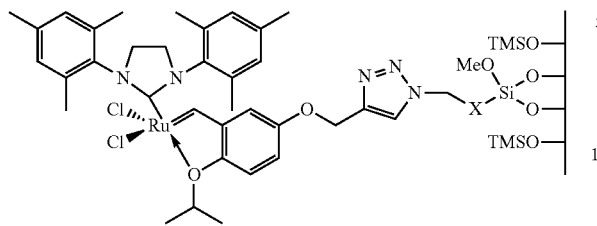

wherein —X— is —CH$_2$CH$_2$— or —C$_6$H$_4$—.

19. The heterogenised catalyst according to claim 16, wherein the organocatalyst is a protonated phenylalanine-derived cyclic amine.

20. The heterogenised catalyst according to claim 16, wherein the organocatalyst is an imidazolidin-4-one.

21. The heterogenised catalyst according to claim 16, which has the formula:

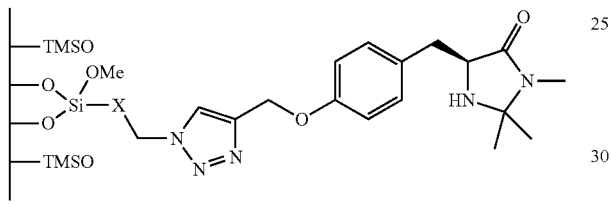

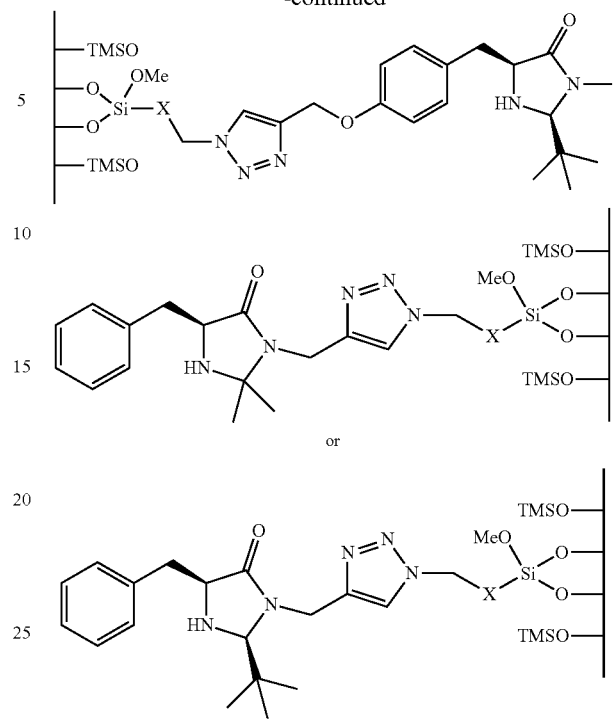

wherein —X— is —CH$_2$CH$_2$— or —C$_6$H$_4$—.

* * * * *

UNITED STATES PATENT AND TRADEMARK OFFICE
CERTIFICATE OF CORRECTION

PATENT NO. : 8,148,287 B2
APPLICATION NO. : 12/532625
DATED : April 3, 2012
INVENTOR(S) : Jackie Y. Ying et al.

Page 1 of 1

It is certified that error appears in the above-identified patent and that said Letters Patent is hereby corrected as shown below:

In the Claims:

Claim 7

Column 19, line 13: "beam" should read -- bears --.

Column 19, line 16: "by way of 1,3-dipolar" should read -- by way of a 1,3-dipolar --.

Claim 15

Column 19, line 60: "converging" should read -- converting --.

Claim 16

Column 20, line 1: "having," should read -- having --.

Signed and Sealed this
Nineteenth Day of March, 2013

Teresa Stanek Rea
*Acting Director of the United States Patent and Trademark Office*